(12) United States Patent
Krasnow et al.

(10) Patent No.: US 10,327,689 B2
(45) Date of Patent: Jun. 25, 2019

(54) AUTOMATED BLOOD SAMPLING DEVICE

(71) Applicant: Verily Life Sciences LLC, Mountain View, CA (US)

(72) Inventors: Benjamin David Krasnow, Redwood City, CA (US); Eric Peeters, San Jose, CA (US); Peter Howard Smith, Pacifica, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 15/660,725

(22) Filed: Jul. 26, 2017

(65) Prior Publication Data

US 2017/0319119 A1    Nov. 9, 2017

Related U.S. Application Data

(63) Continuation of application No. 14/635,643, filed on Mar. 2, 2015, now Pat. No. 9,730,625.

(51) Int. Cl.
*A61B 5/00* (2006.01)
*A61B 5/151* (2006.01)
(Continued)

(52) U.S. Cl.
CPC ........ *A61B 5/15115* (2013.01); *A61B 5/1411* (2013.01); *A61B 5/14532* (2013.01);
(Continued)

(58) Field of Classification Search
CPC . A61B 5/151; A61B 5/15115; A61B 5/15186; A61B 5/150053;
(Continued)

(56) References Cited

U.S. PATENT DOCUMENTS 4,031,889 A   6/1977 Pike
4,243,036 A   1/1981 Ott
(Continued)

FOREIGN PATENT DOCUMENTS

GB    2414186 A    11/2005
JP    2001-511037 T    8/2001
(Continued)

OTHER PUBLICATIONS

International Search Report and Written Opinion for PCT/US2016/015955 dated Aug. 8, 2016.
(Continued)

*Primary Examiner* — Max F Hindenburg
(74) *Attorney, Agent, or Firm* — McDonnell Boehnen Hulbert & Berghoff LLP

(57) ABSTRACT

Devices are provided to automatically access blood from beneath or within skin. These devices include an injector configured to drive a needle into the skin and subsequently to retract the needle from the skin. These devices additionally include a seal to which suction is applied. To drive the needle into the skin, the needle is first driven through the seal, creating at least one hole in the seal. The suction applied to the seal acts to draw blood from the puncture formed in the skin by the needle, through the at least one hole in the seal, and to a sensor, blood storage element, or other payload. These devices can be wearable and configured to automatically access blood from skin, for example, to access blood from the skin at one or more points in time while a wearer of a device is sleeping.

20 Claims, 9 Drawing Sheets

(51) Int. Cl.
*A61B 5/15* (2006.01)
*A61B 5/157* (2006.01)
*A61B 5/145* (2006.01)

(52) U.S. Cl.
CPC ............ *A61B 5/157* (2013.01); *A61B 5/1513* (2013.01); *A61B 5/150022* (2013.01); *A61B 5/150076* (2013.01); *A61B 5/150099* (2013.01); *A61B 5/15109* (2013.01); *A61B 5/15125* (2013.01); *A61B 5/15144* (2013.01); *A61B 5/15151* (2013.01); *A61B 5/15163* (2013.01); *A61B 5/15176* (2013.01); *A61B 5/150213* (2013.01); *A61B 5/150229* (2013.01); *A61B 5/150358* (2013.01); *A61B 5/150412* (2013.01); *A61B 5/150519* (2013.01); *A61B 5/150839* (2013.01); *A61B 5/150854* (2013.01); *A61B 5/150969* (2013.01); *A61B 5/150977* (2013.01); *A61B 5/681* (2013.01)

(58) Field of Classification Search
CPC .......... A61B 5/150221; A61B 5/15022; A61B 5/150076; A61B 5/1411; A61B 5/14532; A61M 5/20; A61M 5/2053; A61M 2005/206; A61M 2005/3112; A61M 5/3123
See application file for complete search history.

(56) References Cited

U.S. PATENT DOCUMENTS

| | | | |
|---|---|---|---|
| 4,547,189 A | 10/1985 | Moore, Jr. | |
| 4,684,366 A | 8/1987 | Denny et al. | |
| 4,684,436 A | 8/1987 | Burns et al. | |
| 4,758,232 A | 7/1988 | Chak | |
| 4,787,398 A | 11/1988 | Garcia et al. | |
| 4,886,499 A | 12/1989 | Cirelli et al. | |
| 5,636,640 A | 6/1997 | Staehlin | |
| 5,662,127 A | 9/1997 | De Vaugnh | |
| 6,045,534 A | 4/2000 | Jacobsen et al. | |
| 6,258,063 B1 | 7/2001 | Haar et al. | |
| 6,340,354 B1 | 1/2002 | Rambin | |
| 6,695,860 B1 | 2/2004 | Ward et al. | |
| 6,896,666 B2 | 5/2005 | Kochamba | |
| 7,001,344 B2 | 2/2006 | Freeman et al. | |
| 7,806,867 B2 | 10/2010 | Willis et al. | |
| 8,808,202 B2 | 8/2014 | Brancazio | |
| 9,039,638 B2 | 5/2015 | Arnitz | |
| 9,113,836 B2 | 8/2015 | Bernstein et al. | |
| 9,174,007 B2* | 11/2015 | Lum | B65B 3/12 |
| 9,295,417 B2 | 3/2016 | Haghgooie et al. | |
| 9,380,972 B2 | 7/2016 | Fletcher et al. | |
| 9,408,568 B2 | 8/2016 | Fletcher et al. | |
| 9,833,183 B2* | 12/2017 | Escutia | A61B 5/150022 |
| 2001/0027328 A1 | 10/2001 | Lum et al. | |
| 2004/0133126 A1 | 7/2004 | McNenny | |
| 2007/0213638 A1 | 9/2007 | Herbrechtsmeier et al. | |
| 2007/0213682 A1 | 9/2007 | Haar et al. | |
| 2009/0124876 A1 | 5/2009 | Nakamura et al. | |
| 2009/0149809 A1 | 6/2009 | Bollenbach et al. | |
| 2009/0306696 A1 | 12/2009 | Doi | |
| 2010/0274202 A1 | 10/2010 | Hyde et al. | |
| 2011/0105952 A1 | 5/2011 | Bernstein et al. | |
| 2011/0217762 A1 | 9/2011 | Viator et al. | |
| 2012/0022499 A1 | 1/2012 | Anderson et al. | |
| 2012/0271123 A1 | 10/2012 | Castle et al. | |
| 2014/0073992 A1 | 3/2014 | Hufford et al. | |
| 2014/0296777 A1 | 10/2014 | Haitsuka et al. | |

FOREIGN PATENT DOCUMENTS

| | | |
|---|---|---|
| JP | 2007-000483 A | 1/2007 |
| JP | 2013-509269 T | 3/2013 |
| WO | 0205890 A2 | 1/2002 |
| WO | 2007/088875 A1 | 8/2007 |
| WO | 2010122222 A2 | 10/2010 |
| WO | 2013182858 | 12/2013 |

OTHER PUBLICATIONS

Cunningham, D.D., et al., "Blood Extraction from lancet wounds using vacuum combined with skin stretching," J. Appl. Physiol., vol. 92, p. 1089-1096 (2002).

Wang, Y., et al., "Electrochemical Sensors for Clinic Analysis," Sensors, vol. 8, p. 2043-2081 (2008).

"Invitation to Pay Additional Fees and, Where Applicable, Protest Fee" prepared by International Searching Authority (EPO), dated on Jun. 2, 2016, issued in connection with International Application No. PCT/US2016/015955, filed on Feb. 1, 2016, 7 pages.

International Search Report of International Application No. PCT/US2016/016367 dated May 30, 2016.

* cited by examiner

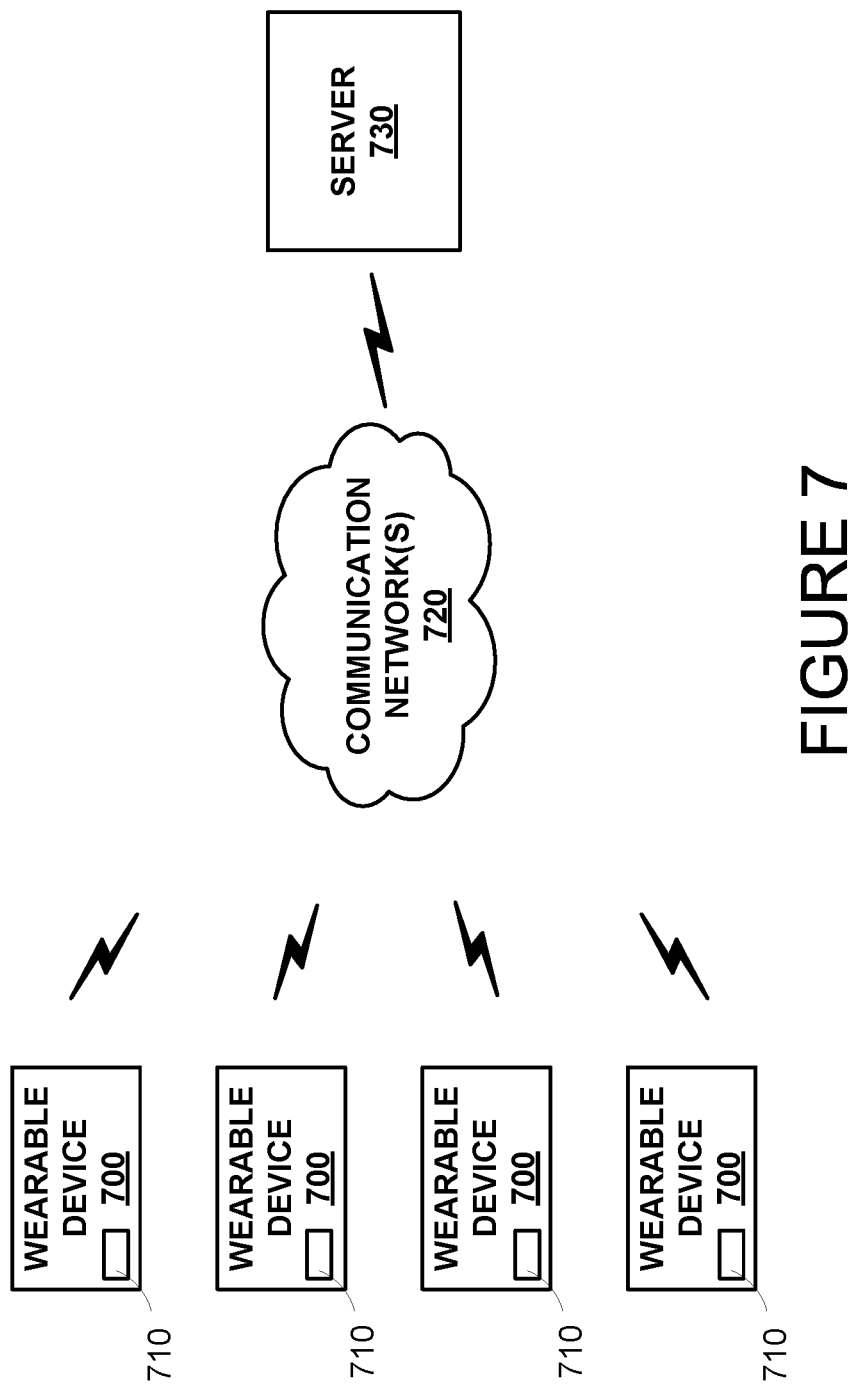

AUTOMATED BLOOD SAMPLING DEVICE

CROSS-REFERENCE TO RELATED APPLICATION

This application claims the benefit of and incorporates by reference the content of U.S. Non-Provisional patent application Ser. No. 14/635,643, filed Mar. 2, 2015.

BACKGROUND

Unless otherwise indicated herein, the materials described in this section are not prior art to the claims in this application and are not admitted to be prior art by inclusion in this section.

Certain medical states or conditions of a human body can be detected by detecting one or more properties of blood in the body. In some examples, such medical states can be detected by extracting a sample of the blood from the body and detecting the one or more properties of the extracted blood using a sensor or other system external to the body. For example, a lancet or other skin-penetrating device could be used to penetrate the skin such that blood is emitted from the skin and/or such that blood can be caused to be emitted from the skin. In another example, a needle, tubing, and other equipment could be used to access blood in an artery or vein of a body. Blood accessed from a body can be exposed to a sensor (e.g., a sensor placed in contact with blood at the surface of skin that has been penetrated). Additionally or alternatively, accessed blood can be stored for later analysis. In a particular example, a lancet can be used to penetrate skin, allowing blood to be emitted from the skin such that a blood glucose level of the blood can be measured using an electrochemical sensor placed in contact with the emitted blood.

SUMMARY

Some embodiments of the present disclosure provide a system including: (i) a needle configured to penetrate skin; (ii) an injector configured to drive the needle into the skin to form a puncture in the skin and subsequently to retract the needle from the skin; (iii) a suction source configured to provide suction; and (iv) a seal configured to receive suction provided by the suction source, wherein the injector is configured to drive the needle through the seal to form at least one hole in the seal, and wherein the suction provided by the suction source is configured to draw blood from the formed puncture in the skin through the formed at least one hole in the seal.

Some embodiments of the present disclosure provide a system including: (i) penetrating means configured to penetrate skin; (ii) injector means configured to drive the penetrating means into the skin to form a puncture in the skin and subsequently to retract the penetrating means from the skin; (iii) suction means configured to provide suction; and (iv) a seal configured to receive suction provided by the suction means, wherein the injector means are configured to drive the penetrating means through the seal to form at least one hole in the seal, and wherein the suction provided by the suction means is configured to draw blood from the formed puncture in the skin through the formed at least one hole in the seal.

Some embodiments of the present disclosure provide a method including: (i) mounting a system to skin, wherein the system comprises: (a) a needle configured to penetrate the skin, (b) an injector, (c) a suction source, and (d) a suction seal configured to receive suction provided by the suction source; and (ii) operating the injector to drive the needle into the skin to form a puncture in the skin and subsequently to retract the needle from the skin, wherein operating the injector to drive the needle into the skin further comprises driving the needle through the seal to form at least one hole in the seal, and wherein the suction provided by the suction source is configured to draw blood from the formed puncture in the skin through the formed at least one hole in the seal.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 7 is a block diagram of an example system that includes a plurality of wearable devices in communication with a server.

DETAILED DESCRIPTION

Figure 1A:
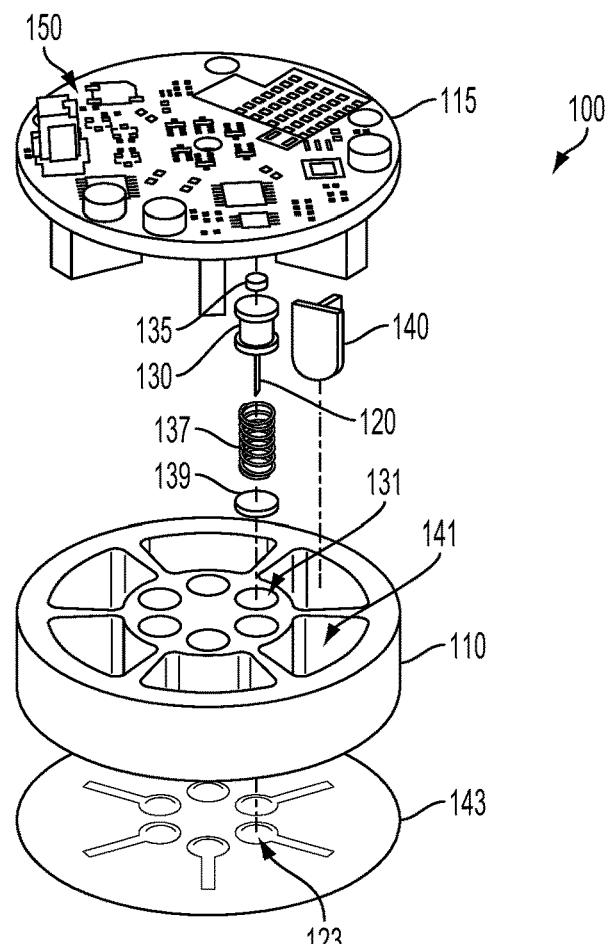
FIG. 1A is an exploded view of an example device.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where the operation of a device to extract a fluid from an environment of interest by piercing a barrier and/or penetrating an element within the environment of interest is desired. The environment may be or include any living or non-living body or a portion thereof, a gel, an emulsion, a fluid conduit, a fluid reservoir, etc.

I. Overview

A body-mountable, wearable, handheld, desktop, or otherwise-configured device may be configured to access blood within a living body (or to access some other fluid in some other environment of interest). Such a blood-accessing device could include means for penetrating or piercing the skin to allow the blood to be emitted from the skin. Such penetrating or piercing means could include one or more needles driven into the skin by an injector incorporating chemical propellants, mechanical or electromechanical elements, or some other elements or components configured to drive the one or more needles into the skin and subsequently to retract the one or more needles from the skin to allow blood to be emitted from the skin via one or more punctures or other penetrations in the skin formed by the one or more needles. Such a blood-accessing device could additionally include suction means for applying suction, through one or more formed holes in a seal, to draw blood into the device to be measured, detected, collected, stored, or otherwise used for some application (e.g., to draw blood into a collection chamber of the device). For example, the blood-accessing device could include a sensor configured to detect glucose in blood received by the device from the skin. Additionally or alternatively, the needle driven into the skin could be a hollow needle, and suction could be applied through the hollow needle to draw blood into the device, through the hollow needle, when the needle is penetrating the skin. A body-mountable blood-accessing device could include multiple needles, injectors, seals, suction sources, sensors, blood storage elements, or other components such that the body-mountable blood-accessing device could be operated to automatically access blood from a wearer at a number of specified points in time, e.g., while the wearer sleeps.

Blood could be accessed by devices and systems described herein for a variety of applications. One or more properties of accessed blood could be measured or detected (e.g., by a sensor of a blood-accessing device, or by some other system that could be exposed to blood accessed and/or stored by such a blood-accessing device). For example, a viscosity of the blood, a concentration or state of one or more analytes in the blood, or some other property of the blood could be detected. For example, a concentration of glucose, of insulin, of one or more hormones, or of some other substance could be detected. Such analytes, and detected concentrations or other properties thereof, could be related to a health state of a person and could be used to determine such a health state. Further, such determined health states could be used to determine and/or indicate some medical or other action to be taken, for example, to take a dose of medicine (e.g., insulin), to perform an exercise, to seek medical attention, or some other action. Additionally or alternatively, detected analyte concentrations or other properties of blood accessed at a plurality of points in time could allow for the determination of one or more physiological baselines or other physiological properties of a person (e.g., a baseline blood glucose concentration, a baseline daily blood glucose profile) and/or the determination and/or modification of a medical treatment regimen (e.g., a timing, dosage, or other property of application of a drug to a person).

An injector or other means configured to drive one or more needles or other means for penetrating skin could be configured in a variety of ways to provide a force to drive the one or more needles into the skin and subsequently retract the one or more needles. For example, the injector could include a piston disposed in a chamber and to which the one or more needles are coupled; a propellant could be used to apply pressure behind the piston to drive the piston, and attached one or more needles, forward such that the one or more needles are driven into the skin. A spring or other means could also be provided to apply a force to retract the one or more needles subsequent to being driven into the skin. In a particular example, the propellant could include a chemical or other material (e.g., nitrocellulose) that could be ignited (e.g., by being heated to an ignition temperature by, e.g., a resistive heating element) to produce gases that could apply pressure on the piston to drive the needle into skin. In another example, the propellant could include compressed gases introduced into the chamber (e.g., by opening a valve, by puncturing a seal, by electrochemically generating the gases, by chemically generating the gases) and the compressed gases could apply pressure on the piston to drive the needle into skin. Additionally or alternatively, an injector could include preloaded springs, magnetic elements coupled to cams, motors, solenoids, ultrasonic vibrators, or other elements configured to drive one or more needles into skin.

A suction source or other suction means configured to provide suction to a seal and to draw blood through one or more holes formed in such a seal (e.g., by one or more needles being driven through the seal) and/or to draw blood into a device by some other means (e.g., through a hollow needle) could provide suction by a variety of mechanisms. In some examples, the suction source could include a pump, an endobaric chemical process, a spring-loaded volume, or some other actuated element(s) configured to be operated to reduce a pressure to which the seal is exposed or to otherwise provide suction to the seal. In some examples, the suction source could include an evacuated volume, i.e., an enclosed volume having a lower pressure than the atmosphere surrounding the device such that, when the seal is breached, blood (or some other fluid or material) is drawn through/toward the one or more holes in the seal.

Such suction provided to a seal and/or through one or more holes formed in the seal could act to draw the skin toward the seal. In some examples, the device could include a concave depression (e.g., a spherical dome depression) formed in the seal and/or in some other element(s) of the device such that the suction provided by the suction source could draw a portion of the skin into the concave depression. Such displacement of the skin could act to increase a rate and/or duration of the emission of blood from the skin. A blood-accessing device could additionally or alternatively be configured in other ways to increase the rate and/or duration of the emission of blood from the skin following penetration by one or more needles. In some examples, heparin or some other anti-clotting or anti-coagulating substance could be introduced on/in the skin (e.g., by being deposited and/or injected by the one or more needles). In some examples, an amount of blood flow in the skin could be increased by, e.g., applying suction to the skin (e.g., using the same or a different suction source as is used to drawn blood through the seal), applying a frictive force to the skin (e.g., by rubbing the skin), and/or heating the skin before driving the one or more needles into the skin.

Blood accessed by devices as described herein (e.g., by driving one or more needles into skin and applying suction to the skin to draw blood out of the skin and into the device) could be used for a variety of applications. In some examples, the device could contain a sensor that could be configured to detect one or more properties of the blood (e.g., to detect the concentration of an analyte in the blood). Such sensors could operate based on contact between the blood and one or more elements of the sensors (e.g., an electrode of an electrochemical sensor). Alternatively, such sensors could be non-contact sensors (e.g., colorimetric or other optical sensors). Sensors could be configured to detect glucose, blood cell counts, electrolytes, hormones, cholesterol, or some other analytes in accessed blood.

Additionally or alternatively, devices as described herein could be configured to store accessed blood for later use, e.g., for interrogation by sensors or other elements of some other devices or systems. For example, devices could access blood from skin and store the accessed blood; later, the stored blood could be presented to a desktop sensor device or to some other system configured to receive the stored blood and to detect one or more properties of the provided blood. Storing blood could include providing heparin or other stabilizing and/or anti-clotting agents such that the blood is stored as a fluid. Additionally or alternatively, accessed, stored blood could be allowed to dry, clot, coagulate, or engage in some other process, and the dried or otherwise altered stored blood could be presented to a sensor device configured to receive the stored blood. In some examples, one or more blood-storing elements of a blood-accessing device could be removable, and could be removed from the device to be presented to another system for analysis (e.g., the removable blood-storing aspects of the device could be removed and sent to a centrally located laboratory).

In some examples, a blood-accessing device may include a user interface that is configured to provide user-discernible indications (e.g., visual, audible, and/or tactile indications) of the operation of the device to access blood and/or information about accessed blood sensed by sensors of the device, progress or other information related to a function of the device, or other information. In some examples, the user interface could additionally provide a means for one or more settings of the device (e.g., timing of one or more future activations of the device to access blood from skin, a user information privacy setting, a user's credentials to access a service) to be specified by a user according to the user's preferences. In some examples, the device may include a wireless communication interface that can transmit/receive data to/from an external device, for example, using Bluetooth, ZigBee, WiFi, and/or some other wireless communication protocol. The data transmitted by the wireless communication interface may include data indicative of one or more physiological parameters or health state measured and/or determined based on blood accessed by the device. The wireless communications interface could additionally or alternatively be configured to receive data from an external system.

It should be understood that the above embodiments, and other embodiments described herein, are provided for explanatory purposes, and are not intended to be limiting. Further, the terms 'access,' 'accessed,' 'accessing,' and any related terms used in relation to the operation of a device to induce emission of blood from skin are used herein (unless otherwise specified) to describe any operation or configuration of a device or system to receive blood from skin or from some other tissue. This could include receiving blood that has been emitted from skin in response to cutting, piercing, incising, cutting, or otherwise penetrating the skin. This could include actively pulling, wicking, suctioning, or otherwise drawing such emitted blood from the skin and/or form the surface of the skin into the device and/or toward some sensor, storage element, or other element(s) of the device. Further, while examples and embodiments described herein refer to accessing blood from skin, it should be understood that methods, devices, and other embodiments described herein could be employed to access other fluids from other environments of interest.

II. Example Operation of Devices to Access Blood

A device could be configured in a variety of ways to access blood from skin or from some other tissue. Such a device could include a variety of penetrating means (e.g., one or more needles) configured to be driven into the skin by injecting means (e.g., by a piston and a chemical propellant) and subsequently retracted from the skin (e.g., by a spring) such that blood can be emitted from the resultant wound (e.g., puncture) in the skin. Further, such devices could include a variety of means (e.g., suction sources, seals, channels, concave depressions) configured to draw blood out of the skin, to draw blood emitted from the skin into the device, and/or to direct such accessed blood toward one or more sensors, blood storage elements, or other elements of the device. Further such devices could include additional elements, sensors, controllers, user interfaces, power sources, communications interfaces or other elements according to an application.

Such blood-accessing devices could be configured to be used to access, detect, store, or otherwise interact with blood in a variety of ways. In some examples, such devices could be configured to be mounted to skin or otherwise worn such that the device can access blood automatically, e.g., a controller or other element(s) of the device could operate an injector of the device to pierce the skin and access blood while a wearer of the device sleeps. Alternatively, the device could be a handheld device configured to be manually mounted to a portion of skin and operated to access blood from the skin. In some examples, the device could be wall-mounted, situated on a desktop, or disposed or mounted in some other way, and mounting the device to skin could include positioning an arm or other aspect of a body proximate to the device (e.g., positioning skin of the wrist of a person proximate to a specified aspect of the device). In some examples, one or more elements (e.g., injectors, needles, seals, suction sources, sensors, blood storage elements) could be removable from the device, e.g., such that other elements of the device (e.g., controllers, user interfaces, mounts) could be reusable by replacing used removable elements of the device.

Blood accessed using devices and methods disclosed herein could be used for a variety of applications. Such applications could include any applications where one or more properties of a person and/or of blood of the person can be detected or determined from a volume of blood accessed using such devices. The volume of blood can be related to the configuration of the device, and could be between approximately one and approximately 10 microliters. For example, the device could be configured to access (e.g., to penetrate the skin and to apply suction to the skin to draw) more than approximately 3 microliters of blood and to detect the concentration of one or more analytes (e.g., glucose, hormones, blood cells) in the accessed blood. The device could be configured (e.g., a stroke length, diameter or shape of a needle, the shape of a concave depression into which skin could be drawn by suction, an amount of applied suction) to provide a specified minimum amount of blood according to a property of the blood to be measured and/or a sensor used to detect such a property. For example, the device could be configured to access sufficient blood to allow detection of a glucose level of the blood using a low-power electrochemical sensor disposed in the device. In another example, the device could be configured to access and store a sufficient amount of blood to allow detection of a property of the blood by some other device or system that is provided with the stored blood from the blood-accessing device.

Figure 1B:
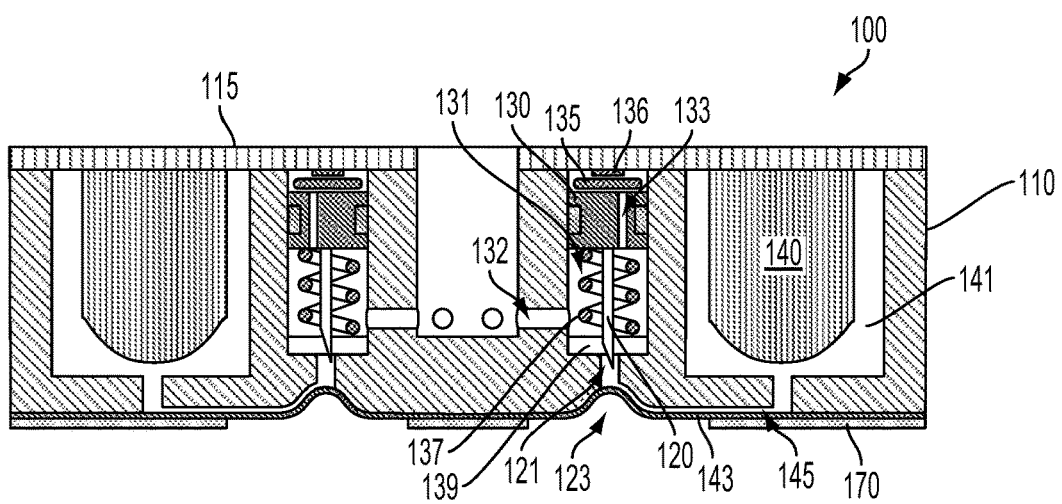
FIG. 1B is a cross-sectional view of the example device of FIG. 1A.

An example of such a blood-accessing device is illustrated in FIGS. 1A and 1B. The device 100 includes six sections, with each section including a respective skin-penetrating needle, injector configured to drive the needle into the skin, suction source and sensor, among other components. FIG. 1A shows an expanded perspective view of components of the first section of the device (components of other section of the device 100 are omitted for illustrative clarity). FIG. 1B is a cross-sectional view of the device 100 illustrated in detail elements of the first section of the device 100. The device 100 includes a housing 110 that is formed to include a number of chambers (e.g., 131) and evacuated volumes (e.g., 141) of the sections as well as other features. Blood-accessing device 100 could be used on its own (e.g., by placing a bottom surface of the device 100 in contact with skin), could be part of another device (e.g., part of a wrist-mountable or otherwise body-mountable device), could be a removable module of another device, or could be configured or operated in some other way.

The first section includes elements disposed within a first chamber 131 formed in the housing 110. The chamber is shown as a cylindrical shape formed in the housing, but could assume other shapes according to an application. The chamber contains a needle 120 configured to penetrate skin, a piston 130 coupled to the needle 120 and configured to slidably move within the chamber 131 (e.g., along the long axis of the chamber 131), and a propellant 135 configured to slidably move the piston 130 within the chamber 131 to drive the needle 120 into skin and further to drive the needle 120 through a seal 143 disposed on a bottom surface of the housing. The chamber additionally contains a spring 137 configured to retract the needle 120 from the skin, a sealant layer 139 that is configured to be pierced by the needle 120 and a resistive element 136 configured to ignite the propellant 135 by providing sufficient heat to the propellant 135 when current passes through the resistive element 136.

The top of the chamber 131 is closed by a circuit board 115 or other member bonded or otherwise adhered to the housing 110. Electronics 150 (e.g., one or more controllers, logic gates, current sources, electronic switches, radio transceivers, analog-to-digital converters) disposed on the circuit board 115 could be configured to perform operations of the device 100, e.g., to apply current to the resistive element 136 (or to other resistive elements or to operate other components of other injectors of the device 100) to ignite the propellant 135 at a specified point in time, to operate a sensor to detect a property of blood accessed from skin by the device 100, or to perform some other operations according to an application.

A needle channel 121 is formed in the bottom of the chamber 131 through the housing 110 such that the needle 120 can be driven into skin proximate the bottom of the housing 110. A piston vent 133 is formed through the piston 130 and chamber vents 132 are formed in the housing 110 to allow gases produced by the ignition of the propellant 135 to be vented out of the device such that the spring 137 can retract the needle 120 subsequent to the ignited propellant 163 causing the piston 130 to drive the needle 120 through the seal 143 and into skin. The diameter, number, geometry, and other properties of the vents 133, 132 could be specified to control a force with which the piston 130 drives the needle 120, a duration of time during which the needle 120 penetrates skin before being retracted by the spring 137, or other properties of operation of the device 100.

The seal 143 includes a concave depression 123 through which the needle 120 penetrates the seal 143 to form a hole in the seal 143 when driven downward by the piston 130. A channel 145 is formed above the concave depression 123 behind the seal 143 and connecting the region behind the seal 143 with an evacuated volume 141 formed in the housing 110. The top of the evacuated volume 141 is sealed by the circuit board 115. Atmospheric gases are prevented from entering the evacuated volume 143 through the chamber 131 by the sealant layer 139 and prevented from entering the evacuated volume 141 through the bottom of the housing 110 (e.g., through the concave depression 123) by the seal 143. A sensor 140 is contained within the evacuated volume 141. The pressure in the evacuated volume 141 is sufficiently lower than the pressure of the environment surrounding the device 100 that, when one or more holes are formed in the seal 143 by the needle 120, the evacuated volume 141 acts as a suction source to draw blood from skin, through the one or more holes in the seal 143, through the channel 145, and into contact with the sensor 140 such that the sensor 140 can detect one or more properties of the blood (e.g., a glucose concentration of the blood). In such an example, the evacuated volume 141 additionally acts as a collection chamber for blood. The evacuated volume 141 could have a pressure less than approximately 50 kilopascals. Other elements of the device 100 (e.g., the channel 145, the concave depression 123, the needle channel 121, a hollow channel formed in a hollow needle of the device (e.g., in examples where the needle 120 is hollow), or some other elements of the device 100 could act as a collection chamber for blood drawn from skin by a suction source.

The device 100 additionally includes a conformal layer 170 configured to conform to the skin such that suction applied by the evacuated volume 141 (or by some other suction source of the device 100) through one or more holes in the seal 143 is applied to skin proximate the one or more holes in the seal 143. This could include the conformal layer 170 including polyurethane, soft rubber, polymeric gel, or some other compliant material. Additionally or alternatively, the conformal layer 170 could include a glue (e.g., cyanoacrylate), a tape, a dry adhesive, or some other adhesive substance.

Figure 2A:
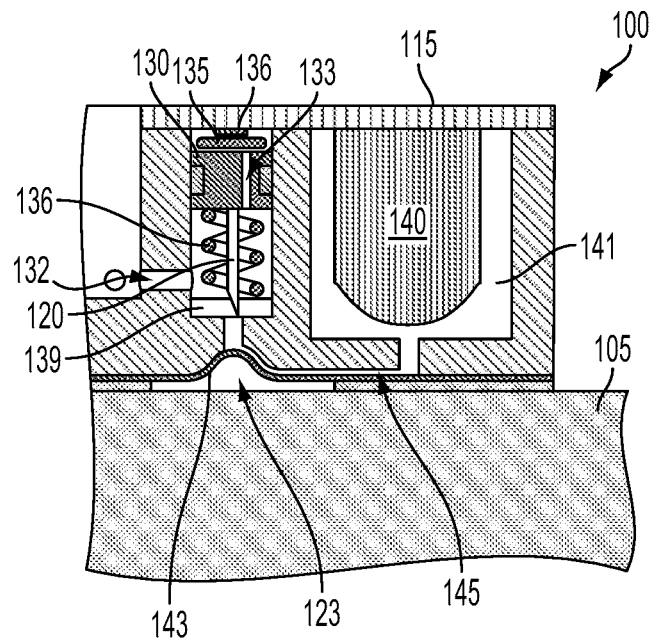
FIG. 2A is a cross-sectional view of an example device mounted to a skin surface.

FIGS. 2A-D illustrate the operation of the device 100 to access blood from skin 105. FIG. 2A shows the device 100 having been mounted to the skin 105; this could include the device 100 being adhered to the skin 105 using an adhesive or mount (e.g., a mount configured to encircle a wrist of a person such that the device 100 is maintained in contact with skin of the wrist). Alternatively, the device 100 could be a handheld device designed to be manually or otherwise maintained in contact with the skin 105. In another example, the device 100 could be a desktop or other relatively immobile device and a body part comprising the skin 105 could be positioned proximate the device 100 as illustrated.

Figure 2B:
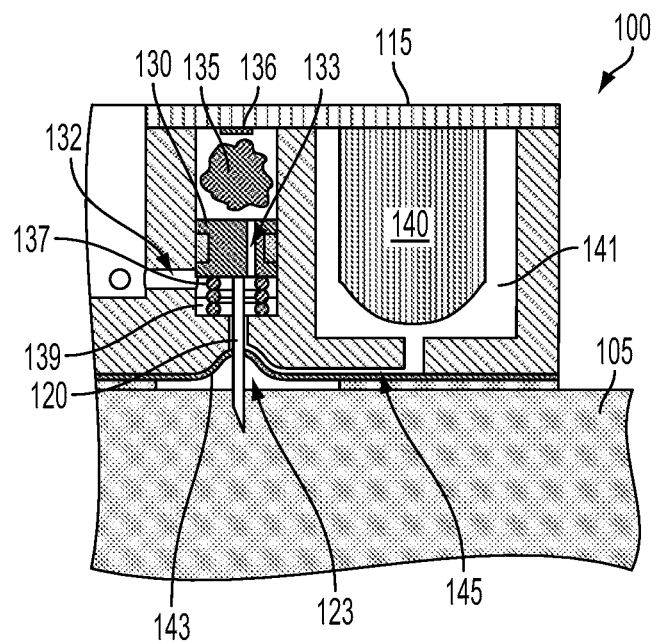
FIG. 2B is a cross-sectional view of the example device of FIG. 2A when a needle of the example device is piercing the skin.

FIG. 2B shows the propellant 135 expanding to slidably move the piston 130 downward, compressing the spring 137 and driving the needle 120 to pierce the seal 143 and further driving the needle 120 into the skin 105. Properties of the spring 137 (e.g., a spring constant, a degree of initial loading), piston 130 (e.g., a mass, a coefficient of friction with the sides of the chamber 131, a diameter and number of piston vents 133), needle 120 (e.g., a diameter, a tip geometry, the presence of a fluoropolymer coating or other anti-friction coating), chamber 131 (e.g., a geometry, a volume of the region above the piston), propellant 135 (e.g., an amount of the propellant, a mix of chemicals comprising the propellant), or other elements of the device 100 could be specified to maximize the speed with which the needle 120 is driven into the skin 105 to, e.g., reduce discomfort induced in a user by operation of the device to penetrate the skin 105.

Figure 2C:
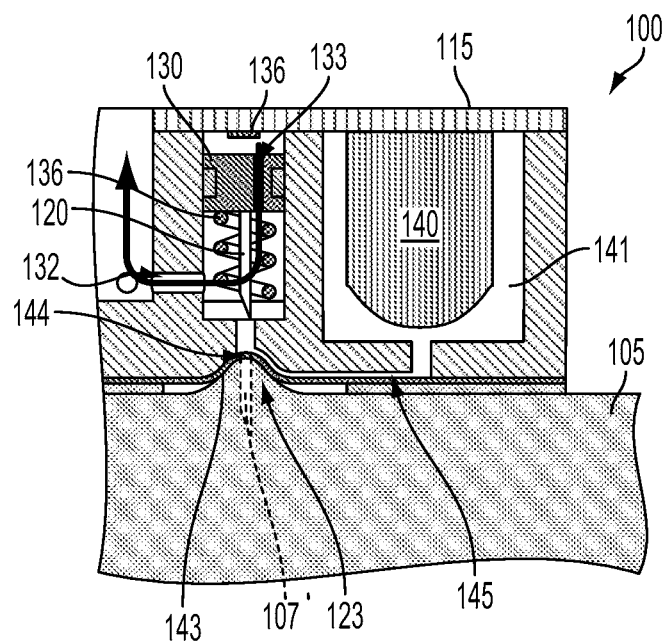
FIG. 2C is a cross-sectional view of the example device of FIG. 2B when the needle of the example device has retracted from the skin.

FIG. 2C shows the piston 130 and needle 120 retracted from the skin 105 partially due to venting of propellant gases through the piston vent 133 and chamber vents 132 (indicated by the arrow) and the force generated by the spring 137 due to compression of the spring 137 by the movement of the piston 130 downward when driving the needle 120 into the skin 105 (shown in FIG. 2B). FIG. 2C additionally shows a hole 144 formed in the seal 143 and a puncture 107 formed in the skin 105 by the piston 130 driving the needle 120 through the seal 143 and into the skin 105. The hole 144 in the seal 143 allows skin proximate the hole 144 (e.g., skin beneath the concave depression 123) to be exposed to suction from the evacuated volume 141. This causes the skin 105 proximate the hole 144 to be drawn up into the concave depression 123. Further, the skin 105 is drawn up into the concave depression 123 such that the puncture 107 is aligned with the hole 144. This could facilitate the drawing of blood from the skin 105 (e.g., from the puncture 107) through the hole 144 into the device 100. In examples where skin is drawn, by suction, toward a device such that a formed puncture in the skin is not aligned with one or more formed holes in a seal, blood could still be drawn into the device, e.g., due to wicking, surface tension, the blood filling the space between the skin and device, or by some other mechanism. Properties of the spring 137, piston 130, needle 120, chamber 131, propellant 135, or other elements of the device 100 could be specified to maximize the speed with which the needle 120 is retracted from the skin 105 and/or minimize the duration during which the needle 120 pierces the skin 105 to, e.g., reduce discomfort induced in a user by operation of the device to penetrate the skin 105. Further, elements of the device 100 could be configured to minimize an amount of blood emitted from the skin 105 that is deposited on the surface of the skin 105 rather than being drawn and/or suctioned into the device 100 (e.g., the device 100 could be configured to suction the skin 105 into contact with the seal 143; the seal 143 could include a hydrophobic or other coating to repel blood).

Figure 2D:
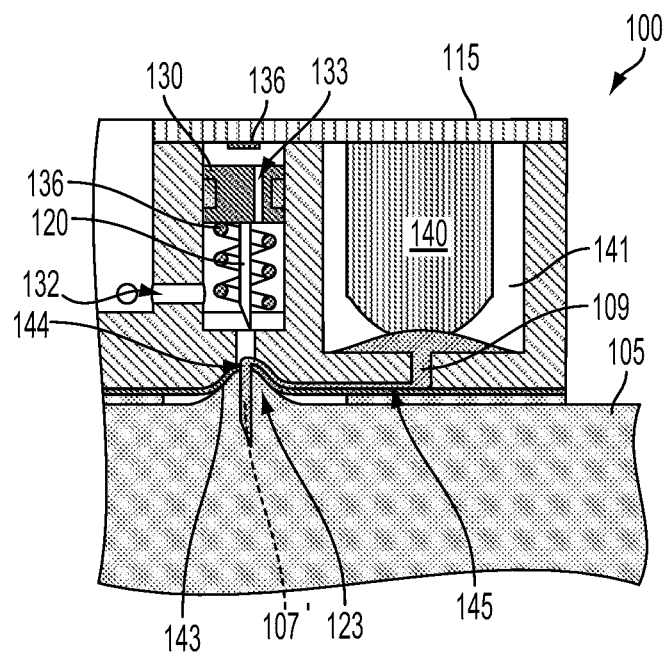
FIG. 2D is a cross-sectional view of the example device of FIG. 2C when blood from the skin has been suctioned to a sensor of the example device.

FIG. 2D shows blood 109 emitted from the skin 105 (e.g., from the puncture 107 formed in the skin 105) that has been drawn through the hole 144 and into the device 100. Further, the emitted blood 109 has been directed, via the channel 145, to the sensor 140. This could include suction from the evacuated volume 141 drawing the blood 109 through the channel 145 to the sensor 140. Additionally or alternatively, the blood 109 could be directed to and/or through the hole 144, through the channel 145, and/or to the sensor 140 by hydrophobic and/or hydrophilic coatings on one or more surfaces of the seal 143, channel 145, or other elements of the device 100. For example, a path from the hole 144 through the channel 145 to the sensor could be coated with a hydrophilic substance; other surfaces of the device 100 that could come into contact with the blood 109 could be coated with a hydrophobic substance. Additionally or alternatively, the channel 145 (or other elements of the device 100) could be sized to direct the blood 109 using capillary action. The channel 145 or other elements of the device 100 could include a coating of heparin or some other pharmaceutical to reduce coagulation and/or clotting of the blood 109 in the device (e.g., to increase the duration and/or amount of blood 109 flowing into the device 100 and/or to the sensor 140).

The shape, size, geometry, or other properties of the concave depression 123 could be specified to maximize an amount of blood emitted from the skin 105 in response to being pierced by the needle 120. For example, the concave depression 123 could have a conical shape. The device 100 could additionally or alternatively be configured in other ways to maximize an amount of blood emitted from the skin 105. For example, the device 100 could be configured to increase blood flow in the skin 109 proximate the device 100 and/or proximate the concave depression 123 by, e.g., heating the skin 105 before penetration, applying a frictive force to the skin before penetration (e.g., by rubbing the skin), applying suction to the skin 105 before penetration, applying a vasodilating, anti-clotting, anti-coagulant, or other pharmaceutical (e.g., heparin, lidocaine) before, during, and/or after penetration of the skin 105, or by being configured or operated in some other way. Pharmaceuticals could be delivered as a coating on the needle 120. Additionally or alternatively, the needle 120 could be hollow and used to deliver a pharmaceutical or other substance and/or to suction blood into the device 100 via such a hollow needle.

Further, the properties of the needle 120 could be specified to maximize the amount of blood emitted from the skin 105, minimize discomfort induced by penetration of the skin, or according to some other consideration. For example, the tip of the needle 120 could include a triple-bevel to minimize deflection of the skin 105 and/or to minimize induced discomfort due to piercing of the skin 105 by the needle 120. Alternatively, the needle 120 could have a chisel tip (e.g., a single bevel), could have a flat 'razor' blade end, could include a taper (e.g., could become thinner toward the end), could be round, flat, or could be configured in some other way to, e.g., maximize blood emitted from the skin 105. The needle 120 could be serrated. The diameter (or gauge) of the needle 120 could be specified to maximize the amount of blood emitted from the skin 105 and/or to minimize discomfort induced by piercing of the skin 105 by the needle 120. For example, the needle 120 could have a gauge between approximately 21 gauge and approximately 36 gauge.

Figure 3:
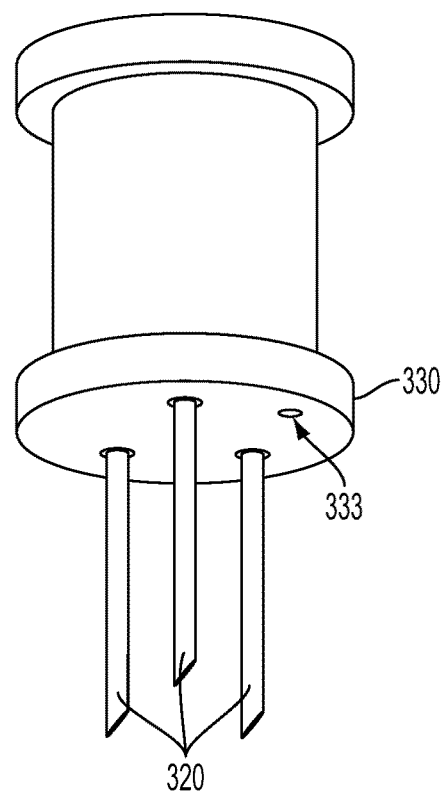
FIG. 3 illustrates an example piston and needles of a device.

In some examples, the piston 130 could drive multiple needles into the skin. FIG. 3 illustrates an example piston 330 that is coupled to three parallel needles 320. The piston 330 additionally includes a piston vent 333. A spacing between the needles 320, a number of the needles 320, the lengths and diameters of the needles 320, the geometry of the tips of the needles 320, or other properties of the needles 320 could be specified to maximize the amount of blood emitted from skin pierced by the needles 320 and/or to minimize discomfort induced by piercing of the skin by the needles 320. For example, the spacing between the needles could be specified to maximize the likelihood of piercing at least one blood vessel in the skin when the piston 330 drives the needles 320 into the skin.

Further, the distance the needle 120 (or needles) pierces into the skin 105 (related, e.g., to properties of the propellant 135, chamber 131, piston 130, spring 137, needle 120, and/or other elements of the device 100) could be specified to maximize the amount of blood emitted from the skin 105 and/or to minimize discomfort induced by piercing of the skin 105 by the needle 120. For example, the device 100 could be configured such that the needle 120 penetrates skin 105 to a depth of approximately 2 millimeters. In some examples, the device 100 could be configured such that the needle 120 penetrates skin 105 to a depth that contains capillaries and/or other blood vessels but that does not contain many nerve endings (e.g., to a depth near the transition between the epidermis and dermis layers of the skin 105). Additionally or alternatively, the device 100 could be configured to drive the needle 120 into the skin 105 at a different angle than the one depicted (i.e., an angle other than approximately 90 degrees).

The propellant 135 could include a variety of chemicals and combinations of chemicals. For example, the propellant 135 could include nitrocellulose, butane, azide, or some other energetic gas-producing substance or other chemical(s). In some examples, the propellant could be formed and/or modified before use, e.g., the propellant could include oxygen and hydrogen formed from water by electrolysis. Alternatively, the propellant could include a compressed gas (e.g., $CO_2$, $N_2$, air compressed by a pump or other means, a gas generated by the device 100 by electrolysis or some other method or means) to which the piston 130 is exposed to drive the needle 120 into the skin 105. Additionally or alternatively, the piston 130 could be driven by a low pressure (e.g., a vacuum, a suction source, an evacuated volume) beneath the piston 130.

The use of the resistive element 136 to ignite the propellant 135 is intended as a non-limiting example. Other means for igniting a chemical propellant (or some other chemical or element of the device 100 according to an application) are anticipated, including but not limited to generating an electrical spark (e.g., by applying a high voltage across a spark gap or between electrodes of the device 100), illuminating the propellant (e.g., using a laser, an LED, or some other light-emitting element(s)), applying a fore and/or vibration to the propellant (e.g., using a piezoelectric elements), or changing a pressure to which the propellant is exposed. Further, the illustrated configuration of the piston 133 and chamber 132 vents are non-limiting examples; more or fewer vents, vents located at different locations, or vents configured in some other way could be included to facilitate a piston driving a needle into skin and/or subsequently retracting the needle from the skin. In an example, one or more of the vents could be normally closed and configured to open (either permanently or temporarily) when a pressure across the vent exceeds some level (e.g., when the pressure behind the piston 130 increases above a specified pressure due to ignition of the propellant 135). Additionally or alternatively, one or more vents could be located in the chamber 131 such that gases behind the piston 130 (e.g., high-pressure gases produced by ignition of the propellant 135) are able to leave the chamber 131 through the vent only when the piston 130 is displaced downward in the chamber 131 by some specified distance.

The piston 130, chamber 131, propellant 135, spring 137, and other elements of the device 100 comprise an injector configured to drive the needle 120 into skin and subsequently to retract the needle from the skin by igniting a chemical propellant. However, the device 100 could include additional or alternative injectors configured to achieve driving of the needle 120 into skin and subsequent retraction thereof. In some examples, the injector could include one or more pre-loaded springs configured to be released (e.g., by a manual button, by a solenoid or other electromechanical actuator). The injector could include one or more magnets and/or cams configured to translate a force between the one or more magnets and other elements of the device 100 to produce driving and/or retracting force(s) that could be applied to the needle 120. In some examples, the injector could include one or more motors or other electromechanical actuator configured to apply driving and/or retracting force(s) directly to the needle (e.g., through a rack-and-pinion mechanism, using a cam, by applying magnetic forces using a solenoid) and/or by charging up a spring (e.g., a rotary spring) that could apply such force(s) to the needle 120. In some examples, the needle 120 could be applied against the skin with a constant force that is less than a force necessary to pierce the skin, and a vibrator (e.g., a vibrating motor, a piezoelectric or otherwise configured ultrasonic transducer) could vibrate the needle 120 such that the needle 120 pierces the skin. Other injectors or other means and methods for driving the needle 120 into the skin and subsequently retracting the needle are anticipated.

Suction applied to the seal 143 could be applied by a variety of means or methods. As illustrated in FIGS. 1 and 2A-D, suction can be provided by an evacuated volume 141 that has a pressure that is lower than the pressure of the atmosphere surrounding the device 100. Additionally or alternatively, suction could be provided by a pump, a chemical process that causes a decrease in pressure (e.g., by causing a decrease in temperature, by consuming nitrogen, oxygen, or some other gas from an enclosed volume (e.g., 141) and/or by changing a phase of such gases), a spring-loaded or otherwise actuated, enclosed volume that can be actuated to increase in size (thus producing suction), or by some other means of producing suction. In some examples, blood emitted from skin (e.g., due to penetration of the skin with a needle as described herein) could be drawn into the device 100, applied to a sensor (e.g., 140), stored, or otherwise manipulated according to an application without using a source of suction, e.g., by using hydrophobic and/or hydrophilic coatings and/or capillary forces to control the location and/or movement of blood within and/or relative to the device 100, by locating a sensor, blood storage element, or other element(s) of the device 100 proximate to the location at which the device 100 pierces the skin with the needle 120, or by configuring the device 100 in some other way. In some examples, e.g., when the needle 120 pierces a vein or other larger vasculature, blood pressure or other forces within or beneath skin may cause a sufficient amount of blood to be emitted from the skin.

When suction is provided by a suction source that comprises an evacuated volume (e.g., 141), a pressure within the evacuated volume could be specified to provide sufficient suction, for example, the pressure within the evacuated volume could be less than approximately 50 kilopascals. Further, the device 100 could be constructed such that the evacuated volume has a pressure less than some maximum value (e.g., 50 kilopascals) for some specified minimum period of time such that the evacuated volume could be used as a suction source to draw blood into the device 100 at a specified future point in time. This could include the device 100 include high-quality seals and adhesives between elements of the device 100 that comprise and/or form the evacuated volume. In some examples, surfaces elements (e.g., the housing 110, the seal 143, the circuit board 115) of the device 100 that are joined to form the evacuated volume could have highly smooth surfaces. In some examples, the device 100 could be configured and/or assembled such that the pressure within the evacuated volume remains below a specified maximum pressure for 48 hours, a week, or some other specified period of time to permit the use of the evacuated volume to provide suction to draw blood into the device 100 at a specified future point in time that is less than the specified period of time. In some examples, this could include storing the device 100 in an evacuated volume of a package (e.g., within an evacuated and sealed blister of packaging material) and removing the device 100 from the evacuated volume of the package before mounting the device 100 to skin.

The seal 143 could be composed of a variety of materials to allow suction to be applied to and contained by the seal 143 until the seal is pierced by the needle 120. Further, the seal 143 could be composed of materials that are capable of being vacuum-formed into a specified shape (e.g., a shape that can be mounted to the housing 110 and that includes one or more concave depressions, e.g., 123). For example, the seal 143 could be composed of polycarbonate.

The sensor 140 could be configured to detect a variety of properties of blood drawn into the device 100 (e.g., 109). For example, the sensor 140 could be configured to detect the presence, concentration, or other properties of an analyte (e.g., glucose, small molecules, cells, cell counts, hormones, cholesterol, testosterone, thyroid hormones, vitamins, minerals, electrolytes, cortisol, creatinine, luteinizing hormone, follicle stimulating hormone) in the blood. In some examples, the sensor 140 could be configured to detect a clotting rate, viscosity, osmolarity, or other property of the blood. The sensor 140 could be configured to detect the property of the blood through direct contact between the blood and one or more elements of the sensor 140. For example, the sensor 140 could be an electrochemical sensor configured to amperometrically, potentiometrically, or otherwise electrochemically detect one or more properties of the blood when the blood comes into contact with one or more electrodes of the electrochemical sensor (e.g., when the blood comes into contact with a working electrode of the sensor 140 that is selectively sensitive to an analyte of interest in the blood and further comes into contact with a reference electrode of the sensor 140). In another example, the sensor 140 could be configured to detect a property of the blood when the blood comes into contact with an analyte-sensitive chemical (e.g., a fluorophore, a chromophore) that has one or more optical properties (e.g., a color, a fluorescence intensity, a fluorescence lifetime) that are related to the analyte in the blood, and the sensor 140 could detect the analyte in the blood by optically interrogating (e.g., illuminating and/or detecting light emitted from) the analyte-sensitive chemical. Additionally or alternatively, the sensor 140 could be configured to detect one or more properties of the blood without being in direct contact with the blood, e.g., by detecting a color of the blood, a property of motion of the blood, or some other property.

Figure 4:
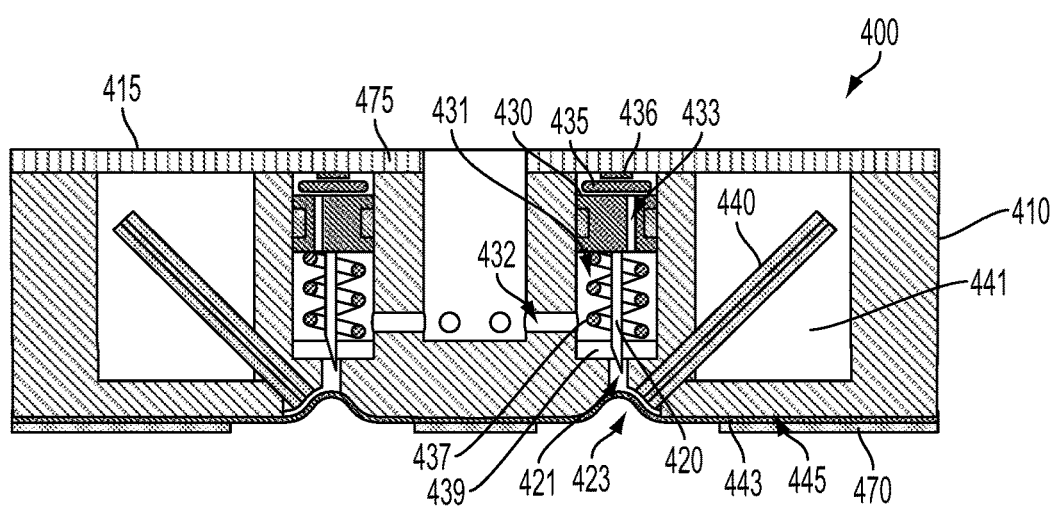
FIG. 4 is a cross-sectional view of an example device.

Additionally or alternatively, a device as described herein could be configured to store blood emitted and/or drawn from skin (e.g., for some later analysis). FIG. 4 shows a cross-sectional view of a device 400 that is configured to be mounted to skin, to pierce the skin with a needle 420, to retract the needle, and to draw blood from the skin into the device 400 and to store the blood in a blood storage element 440. The needle 420 additionally acts to pierce a seal 443 such that suction provided by the device (e.g., by an evacuated volume 441 of the device) can be applied through a formed hole in the seal 443 to draw blood from the skin through the formed hole in the seal 443 and into the blood storage element 440. In the illustrated example, the blood storage element 440 includes a capillary tube, but a blood storage element of a device could additionally or alternatively include an ampoule, a basin, a pit, or some other geometry configured to contain blood. Further, a blood storage element (e.g., 440) could be configured to preserve, chemically modify, prevent clotting or coagulation of, or otherwise manipulate the stored blood. For example, the blood storage element 440 could contain heparin to prevent clotting and/or coagulation of drawn, stored blood. Alternatively, the blood storage element could be configured to allow the blood to dry, according to an application. In some examples, the blood storage element could include an absorptive material, e.g., a piece of fabric configured to absorb blood or other fluids.

Stored blood could be presented to a sensor or other element(s) of a sensing device (e.g., a desktop or other device separate from a blood-accessing device as described herein, e.g., 100, 400) configured to detect one or more properties of the stored blood. For example, a blood-accessing device could be configured to be mounted to such a sensing device and to provide the stored blood to the sensing device. This could include the sensing device detecting one or more properties of the stored blood while it remains in the blood-accessing device (e.g., by optically detecting a property of the stored blood by illuminating and/or receiving light from the stored blood through a window, an optical fiber, or other optically transparent elements of the blood-accessing device). Additionally or alternatively, the blood-accessing device providing the stored blood to a sensing device could include the stored blood being removed from a blood storage element or other components of the blood-accessing device.

A blood-accessing device or system as described herein (e.g., 100, 400) could include multiple sensors, blood-storage elements, needles, injectors, seals, and/or other elements. As illustrated in FIG. 1A, device 100 includes six sections, each section including a respective needle, injector, suction source, and other elements. Each section is configured to drive its respective needle into skin, to subsequently retract the needle from the skin, and the receive blood emitted from the skin in response to being penetrated by the needle. Each section could include one or more sensors, one or more blood storage elements, and/or additional components configured to receive, transmit, measure, modify, or otherwise interact with blood received from the skin. The sections of a device could be similarly configured (e.g., could include similar sensors, be configured to draw similar amounts of blood from skin in a similar manner) or could be differently configured (e.g., different sensors, differently configured injectors, differently configured needles). The sections of a device could be operated to access blood from skin at respective different points in time, e.g., at a number of points in time while a wearer of the device is asleep, at a number of points in time during a week, in response to a command received from a user and/or from a remote system in communication (e.g., wireless communication via Bluetooth, ZigBee, WiFi, or some other wireless communications protocol), in response to a detected command (e.g., a button press) and/or behavior (e.g., performance of an exerting athletic activity, detected using, e.g., an accelerometer of the device 100) of a wearer, based on a detected physiological state of the wearer (e.g., a heart rate or blood pressure detected by sensor(s) of the device 100), or according to some other scheme.

Further, a device could include more or fewer sections, organized similarly or differently (e.g., in a row, rather than circularly as illustrated) than those embodiments illustrated herein. For example, a blood-accessing device could include a single section. In examples wherein the injector and/or suction source are single-use (e.g., wherein the injector ignites a limited supply of a propellant and/or wherein suction is provided by a single evacuated volume) and the device includes a single such section, the blood-accessing device could be configured for a single use. In some examples, such a single and/or limited-use (e.g., six uses, as illustrated in FIG. 1A) could be configured to be a removable and/or replaceable element of some other device. For example, the blood-accessing device 100 could be configured to be removably mounted on or within a body-mountable device (e.g., a wrist-mountable device) that includes a controller, a user interface, a battery, a communications interface, or some other elements. Such a body-mountable device could be configured to operate the limited-use blood-accessing device to access a number of samples of blood from skin (e.g., at respective specified points in time). Once the body-mountable device has operated all of the limited-use sections of the blood-accessing device, the blood-accessing device could be removed from the body-mountable device and replaced. In some examples, the removed blood-accessing device could be configured to store blood, and blood stored in the removed blood-accessing device could be presented to a sensing device for analysis (e.g., the removed blood-accessing device could be sent via post to a sensing device at a laboratory that is remote from a user of the body-mountable device).

Note that the configurations and operations of devices as described herein are meant as non-limiting examples of operation of devices configured to puncture skin and to receive blood emitted from the skin in response to being punctured. Such devices could include a variety of means for penetrating or piercing skin, for driving such penetrating means into skin, for subsequently retracting such penetrating means from the skin, for drawing, wicking, suctioning, or otherwise receiving blood responsively emitted from the skin, for storing the received blood, for sensing one or more properties of the received blood, for moving, directing, preserving, or otherwise interacting with the received blood, or for performing some additional or alternative operations of functions according to an application.

III. Example Wearable Devices

Wearable blood-accessing devices as described herein can be configured to be mounted to an external body surface of a wearer and to enable a variety of applications and functions including accessing blood of the wearer (e.g., drawing, extracting, or otherwise receiving blood), storing such accessed blood, detecting one or more properties of such accessed blood, detecting some other properties of the body of the wearer (e.g., a pulse rate), or performing some other functions. Such wearable devices could enable a variety of applications, including measuring homological properties or other physiological information about a wearer, indicating such measured information or other information to the wearer (e.g., using a vibrator, a screen, a beeper), recording such information, indicating such information to a remote system (e.g., a server in a physician's office), or other functions.

Figure 5A:
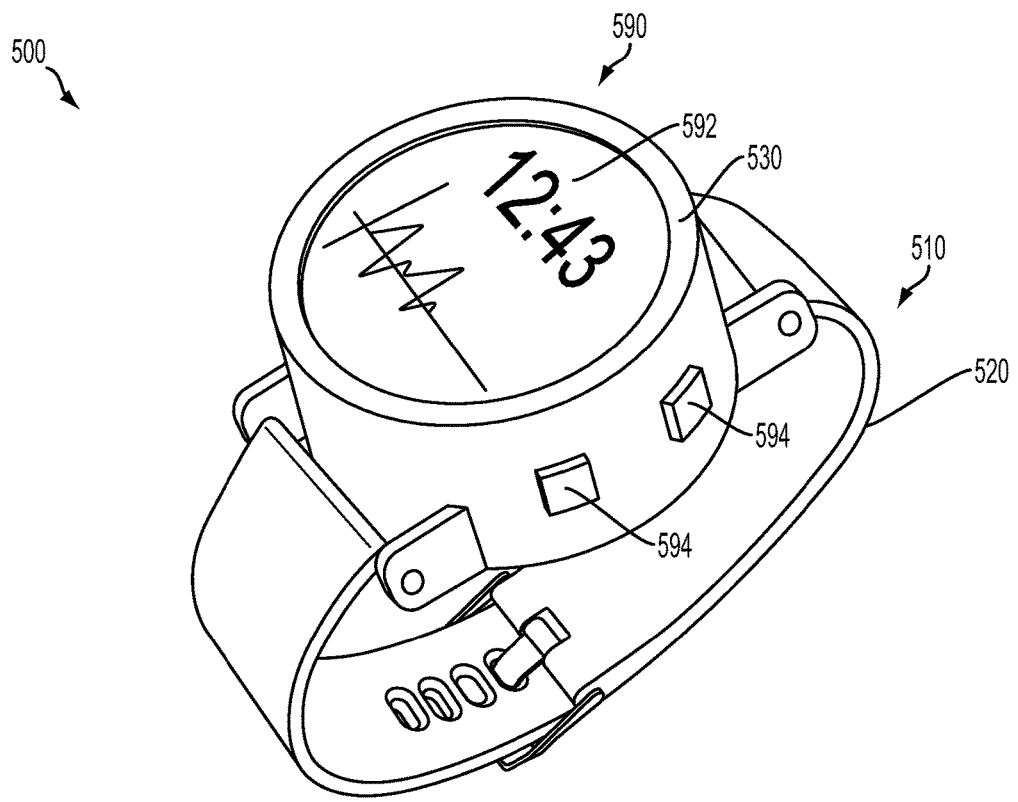
FIG. 5A is a perspective top view of an example body-mountable device.
Figure 5B:
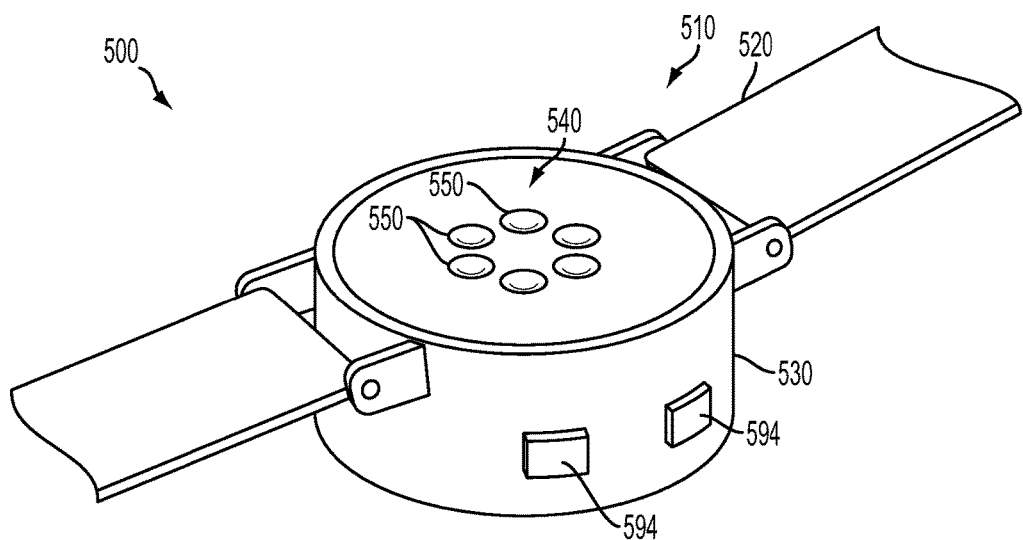
FIG. 5B is a perspective bottom view of the example body-mountable device shown in FIG. 5A.

In some examples, a wearable device 500 (illustrated in FIG. 5) is provided as a wrist-mounted device, as shown in FIGS. 5A and 5B. The wrist-mounted device 500 may be mounted to the wrist of a living subject with a wristband or cuff, similar to a watch or bracelet. The wearable device 500 can be configured to access blood of a wearer and to store, detect a property of, or otherwise interact with such accessed blood. The term "wearable device," as used in this disclosure, refers to any device that is capable of being worn at, on or in proximity to a body surface, such as a wrist, ankle, waist, chest, or other body part. In order to access blood from within and/or beneath skin of the body, the wearable device may be positioned on a portion of the body where subsurface vasculature or other targets or elements of the body of the wearer are easily accessed (e.g., punctured), the qualification of which will depend on the type of system used. A mount 510, such as a belt, wristband, ankle band, etc. can be provided to mount the device at, on or in proximity to the body surface. The mount 510 may prevent the wearable device from moving relative to the body to allow for blood to be drawn from a puncture produced in the skin by the device 500 (e.g., by a driven and subsequently retracted needle of the device) or according to some other application or consideration. In one example, shown in FIGS. 5A and B, the mount 510 may take the form of a strap or band 520 that can be worn around the wrist (or some other part) of the body. Further, the mount 510 may be an adhesive substrate for adhering the blood-accessing device 500 to the body of a wearer.

A housing 530 is disposed on the mount 510 such that it can be positioned on the body. A contact surface 540 of the housing 530 is intended to be mounted facing to the external body surface. The housing 530 may include sensors for detecting one or more physiological properties of the wearer (e.g., a pulse, a blood oxygenation, a galvanic skin response). The contact surface 540 additionally includes a number of concave depressions 550. Each concave depression 550 corresponds to a blood-accessing section of the device 500 that can be operated to drive a needle, through the concave depression (e.g., through a seal of the device and/or through a channel of the device configured to allow the passage of the needle), into skin of a wearer and subsequently to retract the needle from the skin. Further, each section is configured to receive blood responsively emitted from the skin (e.g., by wicking, capillary action, application of suction, or some other means) and to store, detect a property of, or otherwise interact with the received blood.

The housing 530 could be configured to be water-resistant and/or water-proof. That is, the housing 530 could be configured to include sealants, adhesives, gaskets, welds, transparent windows, apertures, press-fitted seams, and/or other joints such that the housing 530 is resistant to water entering an internal volume or volumes of the housing 530 when the housing 530 is exposed to water. The housing 530 could further be water-proof, i.e., resistant to water entering an internal volume or volumes of the housing 530 when the housing 530 is submerged in water. For example, the housing 530 could be water-proof to a depth of 1 meter, i.e., configured to resist water entering an internal volume or volumes of the housing 530 when the housing 530 is submerged to a depth of 1 meter.

The wearable device 500 may also include a user interface 590 via which the wearer of the device may receive one or more recommendations or alerts generated either from a remote server or other remote computing device, or from a processor within the device. The alerts could be any indication that can be noticed by the person wearing the wearable device 500. For example, the alert could include a visual component (e.g., textual or graphical information on a display), an auditory component (e.g., an alarm sound), and/or tactile component (e.g., a vibration). Further, the user interface 590 may include a display 592 where a visual indication of the alert or recommendation may be displayed. The display 592 may further be configured to provide an indication of a measured hemodynamic property of blood accessed from the body of the wearer using the device (e.g., to provide an indication of a blood glucose level of the wearer's blood).

Further, the user interface 590 may include one or more buttons 594 for accepting inputs from the wearer. For example, the buttons 594 may be configured to change the text or other information visible on the display 592. The buttons 594 may be configured to accept inputs for controlling aspects of the data collection system, such as initiating a measurement period (e.g., causing the device 500 to access blood of the wearer by driving a needle into skin or according to some other method), inputs indicating the wearer's current health state (i.e., normal, migraine, shortness of breath, heart attack, fever, "flu-like" symptoms, food poisoning, etc.), or inputs indicating the wearer's activities (e.g., eating a meal, taking a medication).

Note that example devices herein are configured to be mounted to a wrist of a wearer. However, the embodiments described herein could be applied to other body parts (e.g., an ankle, a thigh, a chest, an abdomen, a forehead, a thigh, a finger), or to detect hematological properties or other physiological properties in other environments. For example, embodiments described herein could be applied to detect one or more properties in a target environment (e.g., a natural environment, an environment of an industrial, pharmaceutical, or water treatment process).

Figure 6A:
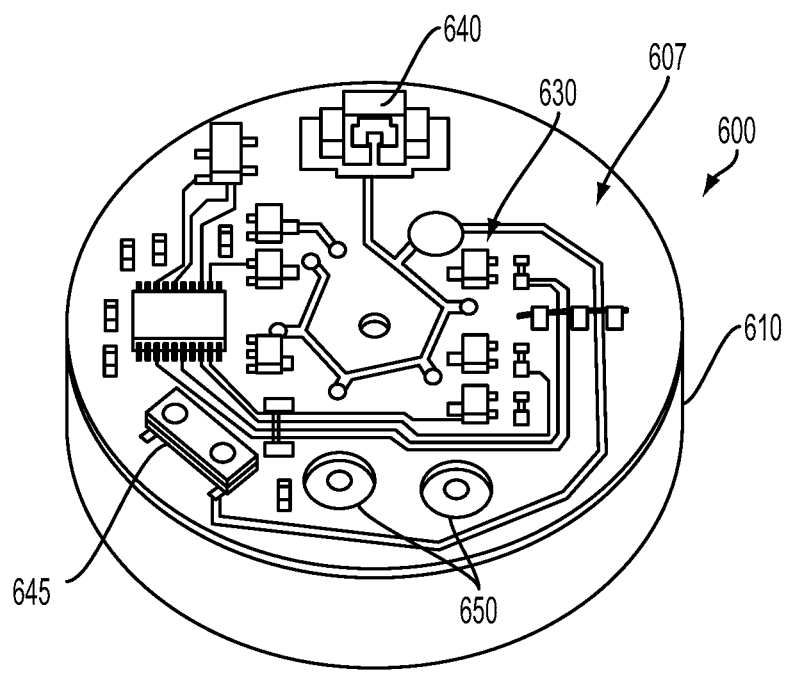
FIG. 6A is a perspective top view of an example body-mountable device.
Figure 6B:
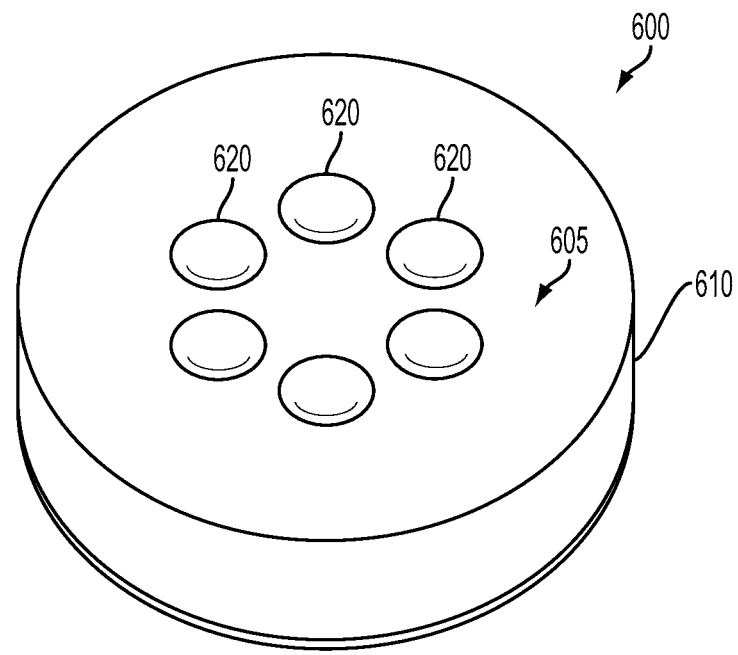
FIG. 6B is a perspective bottom view of the example body-mountable device shown in FIG. 6A.

Blood-accessing sections of the device 500 could be single-use; for example, an injector of one or more sections could ignite a limited supply of a propellant and/or wherein suction is provided for/in a section by a single evacuated volume. In such examples, such single and/or limited-use blood-accessing sections could be configured to be a removable and/or replaceable element of the wearable device 500. For example, FIGS. 6A and 6B show a blood-accessing device 600 that could be configured to be removably mounted on or within the wearable device 500. The blood-accessing device 600 includes a housing 610 that can be positioned on skin of a body when the blood-accessing device 600 is mounted on or within the wearable device 500 and the wearable device 500 is mounted to the body. A contact surface 605 of the housing 610 is intended to be mounted facing to the external body surface. The contact surface 605 includes a number of concave depressions 620. Each concave depression 620 corresponds to a blood-accessing section of the blood-accessing device 600 that can be operated (e.g., when mounted on or within the wearable device 500) to drive a needle, through the concave depression (e.g., through a seal of the device and/or through a channel of the device configured to allow the passage of the needle), into skin of a wearer and subsequently to retract the needle from the skin. Further, each section is configured to receive blood responsively emitted from the skin (e.g., by wicking, capillary action, application of suction, or some other means) and to store, detect a property of, or otherwise interact with the received blood.

The wearable device 500 could be configured to operate the blood-accessing device 600 to access a number of samples of blood from skin (e.g., at respective specified points in time). Once the body-mountable device has operated all of the sections of the blood-accessing device 600, the blood-accessing device 600 could be removed from the wearable device 500 and replaced. In some examples, this could include operating one or more injectors, suction sources, and/or other components of the blood-accessing device 600 (e.g., via electrical connector 640, optical receiver/transmitter 645, and/or electronics 630). Additionally or alternatively, the wearable device 500 could operate the blood-accessing device 600 using other means, e.g., by igniting propellant of the blood-accessing device 600 by heating the propellant using a laser of the wearable device 500.

In some examples, the removed blood-accessing device 600 could be configured to store blood, and blood stored in the removed blood-accessing device 600 could be presented to a sensing device for analysis (e.g., the removed blood-accessing device 600 could be sent via post to a sensing device at a laboratory that is remote from a user of the body-mountable device 500). For example, samples of blood stored within the blood-accessing device 600 could be accessed via ports 650 of the blood-accessing device 600.

Additionally or alternatively, the wearable device 500 could be configured to detect one or more properties of the blood accessed using the blood-accessing device 600. In some examples, the blood-accessing device 600 could include one or more sensors configured to detect one or more properties of blood. The wearable device 500 could operate the sensors of the blood-accessing device 600 (e.g., via electrical connector 640, optical receiver/transmitter 645, and/or electronics 630. Additionally or alternatively, the wearable device 500 could be configured to illuminate and/or receive light emitted from the blood-accessing device 600 (e.g., to illuminate and/or receive light emitted from an analyte-sensitive chemical that has one or more optical properties that is related to the analyte in the blood), via a window, optical fiber, or other optically transparent element(s) of the blood-accessing device 600) to detect one or more properties of the blood drawn, wicked, suctioned, or otherwise received from skin by the blood-accessing device 600.

Wearable blood-accessing devices and other embodiments as described herein can include a variety of components configured in a variety of ways. Devices described herein could include electronics including a variety of different components configured in a variety of ways to enable applications of the wearable device. The electronics could include controllers, amplifiers, switches, display drivers, touch sensors, wireless communications chipsets (e.g., Bluetooth radios or other radio transceivers and associated baseband circuitry to enable wireless communications between the wearable device and some other system(s)), or other components. The electronics could include a controller configured to operate one or more sensors, injectors, suction sources, and/or components of a blood-accessing device to detect one or more hematological or other properties of a body and/or to access and store or otherwise interact with blood from within and/or beneath skin of the body. The controller could include a processor configured to execute computer-readable instructions (e.g., program instructions stored in data storage of the wearable device) to enable applications of the wearable device. The electronics can include additional or alternative components according to an application of the wearable device.

Wearable or otherwise-configured blood-accessing devices as described herein could include one or more user interfaces. A user interface could include a display configured to present an image to a wearer and to detect one or more finger presses of a wearer on the interface. The controller or some other component(s) of the electronics could operate the user interface to provide information to a wearer or other user of the device and to enable the wearer or other user to affect the operation of the wearable device, to determine some property of the wearable device and/or of the wearer of the wearable device (e.g., a hematological property of blood and/or a health state of a wearer of the wearable device), or to provide some other functionality or application to the wearer and/or user. As one example, the wearer could press an indicated region of the user interface to indicate that the wearable device should begin logging detected medical information about the wearer. Other indicated information, changes in operation of the wearable device, or other functions and applications of the user interface are anticipated.

Note that the embodiments illustrated in the Figures are illustrative examples and not meant to be limiting. Alternative embodiments, including more or fewer components in alternative configurations are anticipated. A wearable, handheld, body-mountable, desktop, or otherwise configured device could include multiple housings or other such assemblies each containing some set of components to enable applications of such a device. A blood-accessing device as described herein could be configured to perform a variety of functions and to enable a variety of applications. Blood-accessing devices could be configured to operate in concert with other devices or systems; for example, blood-accessing devices could include a wireless communication interface configured to transmit data indicative of one or more properties of the blood of a wearer of the wearable device. Other embodiments, operations, configurations, and applications of a blood-accessing device as described herein are anticipated.

FIG. 7 is a simplified schematic of a system including one or more wearable blood-accessing devices 700. The one or more wearable devices 700 may be configured to transmit data via a communication interface 710 over one or more communication networks 720 to a remote server 730. In one embodiment, the communication interface 710 includes a wireless transceiver for sending and receiving communications to and from the server 730. In further embodiments, the communication interface 710 may include any means for the transfer of data, including both wired and wireless communications. For example, the communication interface may include a universal serial bus (USB) interface or a secure digital (SD) card interface. Communication networks 720 may be any one of may be one of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 700 transmits data to a mobile phone or other personal computing device, which in turn transmits the data to the server 730.

In some examples, multiple wearable devices 700 could be configured to access blood from and/or detect multiple hematological or other properties of a single wearer. For example, the single wearer could wear or otherwise operate two or more wearable devices 700 to measure respective hematological or other physiological properties from respective two or more portions of the body of the wearer (e.g., respective portions of subsurface vasculature of the wearer) and/or during different periods of time (e.g., the wearable devices 700 used by the wearer could be limited-use devices, e.g., each including a discrete number of single-use blood-accessing sections).

In addition to receiving communications from the wearable device 700, such as collected hematological properties or other collected physiological properties and data regarding health state as input by the user and/or one or more properties of a wearer detected using a sensor disposed in the wearable device 700, the server may also be configured to gather and/or receive either from the wearable device 700 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the hematological property data and the indicated health state of the user. From this information, the server may be configured to derive an indication of the effectiveness of the drug or treatment. For example, if a drug is intended to control a blood sugar of a wearer and the wearer of the device does not indicate that they are experiencing nausea, lightheadedness, or other sequelae after beginning a course of treatment with the drug, the server may be configured to derive an indication that the drug is effective for that wearer.

Further, some embodiments of the system may include privacy controls which may be automatically implemented or controlled by the wearer of the device. For example, where a wearer's collected hematological property data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and hematological properties, collected from his or her device may only be used for generating an individual baseline and recommendations in response to collection and comparison of his or her own data and may not be used in generating a population baseline or for use in population correlation studies.

IV. Example Electronics

Figure 8:
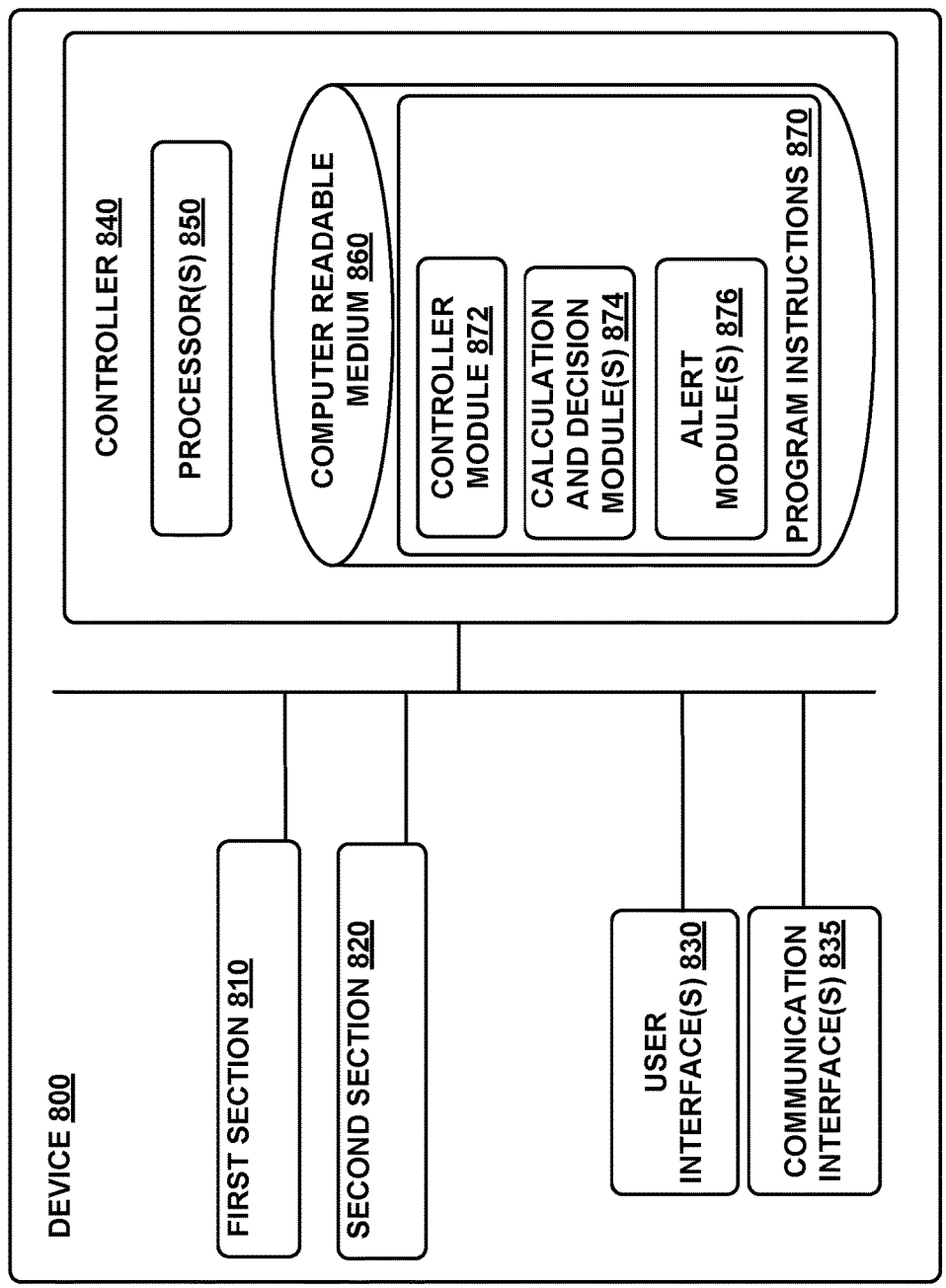
FIG. 8 is a functional block diagram of an example device.

FIG. 8 is a simplified block diagram illustrating the components of a device 800, according to an example embodiment. Device 800 may take the form of or be similar to one of the blood-accessing devices 100, 400, 500, 600 shown in FIGS. 1, 2A-D, 4, 5A-B, and 6A-B. However, device 800 may also take other forms, such as an ankle, waist, or chest-mounted device. Device 800 could also take the form of a device that is not configured to be mounted to a body. For example, device 800 could take the form of a handheld device configured to be maintained in proximity to skin by a user or operator of the device 800 or by a frame or other supporting structure. Device 800 also could take other forms.

In particular, FIG. 8 shows an example of a device 800 having first 810 and second 820 blood-accessing sections, a user interface 830, communication interface 835 for transmitting data to a remote system, and a controller 840. The components of the device 800 may be disposed on a mount or on some other structure for mounting the device to enable stable collection of blood emitted from skin in response to penetration of the skin by one or more needles of the device 800, for example, mounting to an external body surface where one or more portions of subsurface vasculature or other anatomical elements are readily accessible.

Controller 840 may be provided as a computing device that includes one or more processors 850. The one or more processors 850 can be configured to execute computer-readable program instructions 870 that are stored in the computer readable data storage 860 and that are executable to provide the functionality of a device 800 described herein.

The computer readable medium 860 may include or take the form of one or more non-transitory, computer-readable storage media that can be read or accessed by at least one processor 850. The one or more computer-readable storage media can include volatile and/or non-volatile storage components, such as optical, magnetic, organic or other memory or disc storage, which can be integrated in whole or in part with at least one of the one or more processors 850. In some embodiments, the computer readable medium 860 can be implemented using a single physical device (e.g., one optical, magnetic, organic or other memory or disc storage unit), while in other embodiments, the computer readable medium 860 can be implemented using two or more physical devices.

First 810 and second 820 blood-accessing sections could include any components configured to drive a needle into skin, to subsequently retract the needle from the skin, to receive blood from the resulting puncture in the skin (e.g., by applying suction to the skin), and to perform other functions as described elsewhere herein. Blood-accessing sections could include motors, piezoelectric transducers, solenoids, actuated valves, resistive heaters or other propellant-igniting components, or other components of an injector configured to drive a needle into skin and/or to subsequently retract such a needle. Blood-accessing sections 810, 820 could include blood-storage elements as described elsewhere herein to store blood for, e.g., later analysis. Blood-accessing sections 810, 820 could include sensors configured to detect a variety of properties of blood drawn, wicked, suctioned, received, or otherwise accessed by the blood-accessing sections 810, 820. Blood-accessing sections 810, 820 could include pumps of other elements (e.g., evacuated volumes) configured to provide suction (e.g., to draw skin toward and/or into concave depressions of the blood-accessing sections 810, 820, to draw blood from the skin into the device 800, to direct blood from within the device, 800, e.g., to one or more sensors, blood-storage elements, or other components of the device 800). The device 800 could include additional (or fewer) blood-accessing sections. The blood-accessing sections 810, 820 could be similarly or differently configured. The blood-accessing sections 810, 820 could be part of a removable and/or replaceable portion of the device 800. The device 800 may include further sensors (not shown), e.g., heart rate sensors, galvanic skin response sensors, pulse oximeters, or other sensors configured to detect one or more properties of the body of a wearer and/or of the environment of the device 800.

The program instructions 870 stored on the computer readable medium 860 may include instructions to perform any of the methods described herein. For instance, in the illustrated embodiment, program instructions 870 include a controller module 872, calculation and decision module 874 and an alert module 876.

Calculation and decision module 874 may include instructions for operating the blood-accessing sections 810, 820 and analyzing data generated by the blood-accessing sections 810, 820 (e.g., by sensors thereof) to determine one or more hematological properties of blood or other information (e.g., health states) of a body of a wearer of the device 800, such as a blood glucose level at a number of points in time. Calculation and decision module 874 can additionally include instructions for analyzing the data to determine if a medical condition or other specified condition is indicated, or other analytical processes relating to the environment proximate to the device 800 (e.g., based on information generated by additional sensors of the device 800). In particular, the calculation and decision module 874 may include instructions for operating the first 810 and second 820 blood-accessing sections to access blood (e.g., for operating resistive heating elements of the blood-accessing sections 810, 820 to ignite propellant and drive respective needles into skin) at respective specified points in time (e.g., points in time while a wearer sleeps, points in time during the week).

The controller module 872 can also include instructions for operating a user interface 830. For example, controller module 872 may include instructions for displaying data collected by the blood-accessing sections 810, 820 and analyzed by the calculation and decision module 874, or for displaying one or more alerts generated by the alert module 876. Controller module 872 may include instructions for displaying data related to a detected hematological property of accessed blood and/or a determined health state of a wearer. Further, controller module 872 may include instructions to execute certain functions based on inputs accepted by the user interface 830, such as inputs accepted by one or more buttons disposed on the user interface (e.g., to operate one or both of the blood-accessing sections 810, 820 to access blood from a wearer and/or to detect one or more properties of the accessed blood in response to an input from the user).

Communication platform 835 may also be operated by instructions within the controller module 872, such as instructions for sending and/or receiving information via a wireless antenna, which may be disposed on or in the device 800. The communication interface 835 can optionally include one or more oscillators, mixers, frequency injectors, etc. to modulate and/or demodulate information on a carrier frequency to be transmitted and/or received by the antenna.

In some examples, the device 800 is configured to indicate an output from the processor by modulating an impedance of the antenna in a manner that is perceivable by a remote server or other remote computing device.

The program instructions of the calculation and decision module 874 may, in some examples, be stored in a computer-readable medium and executed by a processor located external to the device 800. For example, the device 800 could be configured to collect certain data regarding hematological properties from the user and then transmit the data to a remote server, which may include a mobile device, a personal computer, the cloud, or any other remote system, for further processing.

The computer readable medium 860 may further contain other data or information, such as medical and health history of a user of the device 800, that may be useful in determining whether a medical condition or some other specified condition is indicated. Further, the computer readable medium 860 may contain data corresponding to certain physiological parameter baselines, above or below which a medical condition is indicated. The baselines may be pre-stored on the computer readable medium 860, may be transmitted from a remote source, such as a remote server, or may be generated by the calculation and decision module 874 itself. The calculation and decision module 874 may include instructions for generating individual baselines for the user of the device 800 based on data collected based on a certain number of blood samples accessed using blood-accessing elements (e.g., 810, 820) of the device 800. Baselines may also be generated by a remote server and transmitted to the device 800 via communication interface 830. The calculation and decision module 874 may also, upon determining that a medical or other emergency condition is indicated, generate one or more recommendations for the user of the device 800 based, at least in part, on consultation of a clinical protocol. Such recommendations may alternatively be generated by the remote server and transmitted to the device 800.

In some examples, the collected hematological property data, baseline profiles, health state information input by device users and generated recommendations and clinical protocols may additionally be input to a cloud network and be made available for download by a user's physician. Trend and other analyses may also be performed on the collected data, such as hemodynamic property data and health state information, in the cloud computing network and be made available for download by physicians or clinicians.

Further, hematological property and health state data from individuals or populations of device users may be used by physicians or clinicians in monitoring efficacy of a drug or other treatment. For example, high-density, real-time data may be collected from a population of device users who are participating in a clinical study to assess the safety and efficacy of a developmental drug or therapy. Such data may also be used on an individual level to assess a particular wearer's response to a drug or therapy. Based on this data, a physician or clinician may be able to tailor a drug treatment to suit an individual's needs.

In response to a determination by the calculation and decision module 874 that a medical or other specified condition is indicated (e.g., that a wearer is hyperglycemic or hypoglycemic, based on a detected glucose level of blood accessed from the body of the wearer), the alert module 876 may generate an alert via the user interface 830. The alert may include a visual component, such as textual or graphical information displayed on a display, an auditory component (e.g., an alarm sound), and/or tactile component (e.g., a vibration). The textual information may include one or more recommendations, such as a recommendation that the user of the device contact a medical professional, deliver a dose of a pharmaceutical (e.g., insulin), seek immediate medical attention, or administer a medication.

V. Example Methods

Figure 9:
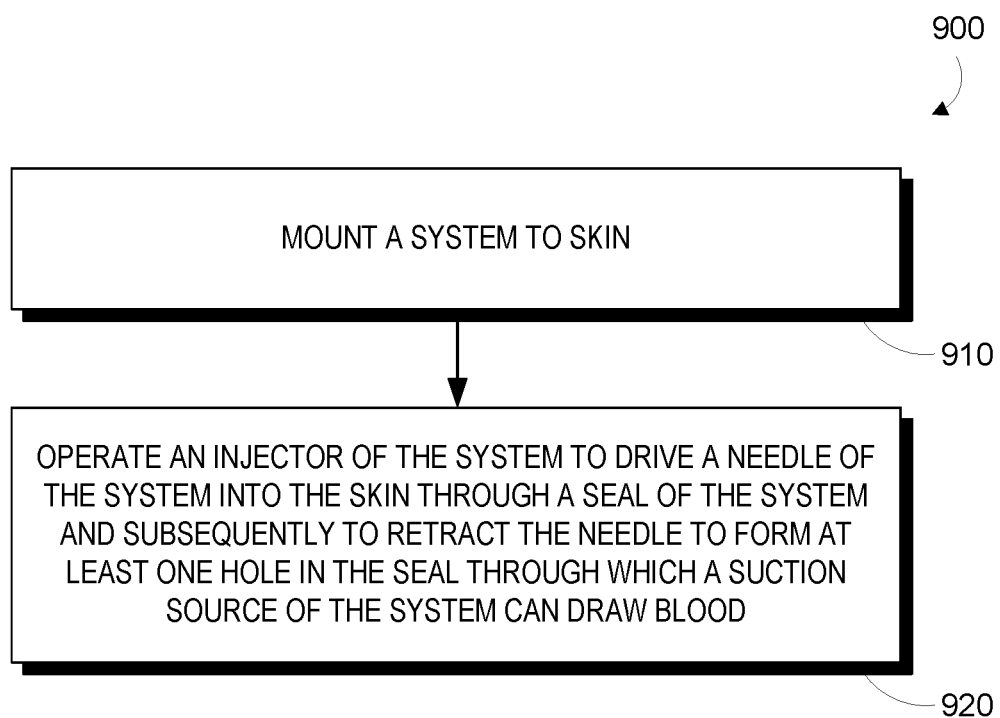
FIG. 9 is a flowchart of an example method.

FIG. 9 is a flowchart of a method 900 for operating a blood-accessing system. The operated system includes: (i) a needle configured to penetrate skin, (ii) an injector, (iii) a suction source, and (iv) a seal configured to receive suction provided by the suction source. The method 900 includes mounting the system to skin (910). The system could be a wearable device and mounting the system to skin (910) could include mounting the system to and/or around a part of a body using a strap, adhesive, or some other means. The system could be a handheld device and mounting the system to skin (910) could include manually or otherwise positioning the system proximate skin. The system could be a desktop device, a wall- or ceiling-mounted device, or some other form of stationary device and mounting the system to skin (910) could include positioning a body part having the skin (e.g., a wrist, and arm) proximate the system.

The method 900 also includes operating the injector to drive the needle into the skin through the seal and subsequently to retract the needle to form at least one hole in the seal through which the suction source can draw blood (920). This could include operating the injector at a specified point in time and/or in response to a command (e.g., a command received through a user interface of the system, a command generated by the system in reasons to detecting that skin is present proximate the system, a command generated by a remote system in communication with the blood-accessing system). Operating the injector (920) could include igniting a propellant, e.g., by heating the propellant using a resistive heating element. Additionally or alternatively, operating the injector (920) could include operating a motor, solenoid, piezoelectric transducer, or other elements of the system and/or of the injector.

The system could include one or more sensors configured to detect one or more properties of blood accessed by the system and the method 900 could include operating the sensor to detect the one or more properties of the blood (e.g., to detect a glucose concentration in the blood). Additionally or alternatively, the system could include one or more blood storage elements configured to receive and store blood accessed by the system and the method 900 could include storing the accessed blood. The method 900 could further include providing blood stored by the blood storage element to a sensing device and operating the sensing device to detect a property of the blood provided to the sensing device. In some examples, one or more elements, sections, or portions of the system (e.g., a section configured to drive a needle into skin, subsequently retract the needle, and to apply suction to the skin to draw blood into the section) could be removable, and the method 900 could include removing and replacing such elements, sections, or portions subsequent to operating such elements, sections, or portions to access blood from skin.

The method 900 could include additional or alternative steps. The method 900 could include heating, applying suction to, or otherwise preparing a portion of skin to emit blood in response to being pierced by a needle of the system. In some examples, the method 900 could include transmitting (e.g., wirelessly transmitting, transmitting via a Bluetooth wireless link, transmitting via a cable, transmitting via the internet or some other network) information indicative of a detected hematological property of blood accessed by the system. In some examples, the method 900 could include determining a health state of the wearer based on a hematological property detected from blood accessed by the system. In some examples, the method 900 could include indicating a detected hematological properties to a user via a user interface of the system and/or indicating such information to a remote system (e.g., to a physician's computer, via a wireless or other communications link).

The example method 900 illustrated in FIG. 9 is meant as an illustrative, non-limiting example. Additional or alternative elements of the method and additional or alternative components of the system are anticipated, as will be obvious to one skilled in the art.

VI. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:
a needle;
a chamber, wherein the needle is disposed at least partially within the chamber;
a propellant disposed within the chamber;
a piston disposed within the chamber, wherein the needle is coupled to the piston, wherein the piston is configured to slidably move within the chamber, wherein the propellant is ignitable to slidably move the piston within the chamber to drive the needle into skin to form a puncture in the skin, wherein the piston includes a vent, wherein the vent is configured to allow gases produced by ignition of the propellant to vent through the piston.

2. The system of claim 1, further comprising a spring, wherein the spring is coupled to the piston, wherein the piston slidably moving within the chamber to drive the needle into skin compresses the spring such that, subsequent to the needle being driven into the skin, the spring exerts a force to retract the needle from the skin.

3. The system of claim 1, wherein the chamber comprises a further vent, wherein the further vent is configured to allow gases produced by ignition of the propellant to vent through the further vent into an environment of the system.

4. The system of claim 1, further comprising:
a resistive heating element; and
a controller, wherein the controller is configured to operate the resistive heating element to ignite the propellant.

5. The system of claim 4, further comprising a printed circuit board, wherein the chamber is formed in a housing, wherein the chamber is closed by a circuit board adhered to the housing, and wherein the resistive heating element is disposed on the printed circuit board.

6. The system of claim 1, further comprising:
a light source; and
a controller, wherein the controller is configured to operate the light source to ignite the propellant.

7. The system of claim 1, wherein the propellant comprises nitrocellulose.

8. The system of claim 1, further comprising:
a suction source; and
a seal, wherein the seal is coupled to the suction source such that the seal receives suction provided by the suction source, wherein the propellant is ignitable to slidably move the piston within the chamber to drive the needle through the seal to form a hole in the seal when the seal is receiving suction provided by the suction source, and wherein the suction provided by the suction source is sufficient to draw blood from a formed puncture in the skin through the formed hole in the seal.

9. The system of claim 8, wherein the suction source comprises an evacuated volume.

10. The system of claim 8, wherein the suction source comprises an evacuated volume having a pressure less than approximately 50 kilopascal.

11. The system of claim 8, wherein the seal comprises a concave depression, wherein the propellant is ignitable to slidably move the piston within the chamber to drive the needle through the concave depression of the seal to form a hole in the seal, and wherein the suction provided by the suction source is sufficient to suction the skin into the concave depression.

12. The system of claim 8, further comprising a blood storage element, wherein the suction provided by the suction source is sufficient to draw blood through the formed hole in the seal to the blood storage element, and wherein the blood storage element is configured to store blood drawn by the suction to the blood storage element.

13. The system of claim 8, further comprising a sensor, wherein the sensor is configured to detect a property of blood to which the sensor is exposed, wherein the suction provided by the suction source is sufficient to draw blood through the formed hole in the seal to the sensor.

14. The system of claim 8, further comprising a conformal layer, wherein the conformal layer is configured to conform to the skin such that the suction provided by the suction source through the formed hole in the seal applies suction to the skin proximate the hole in the seal.

15. The system of claim 1, wherein the system comprises a body-mountable device, wherein the body-mountable device is configured to be mounted to a surface of the skin.

16. The system of claim 15, wherein the needle, piston, chamber, and propellant are disposed in a first sampling section of the body-mountable device, and wherein the body-mountable device further comprises one or more additional sampling sections, each additional sampling section including a respective needle, piston, chamber, and propellant.

17. A method comprising:
mounting a system to skin, wherein the system comprises:
 a needle;
 a chamber, wherein the needle is disposed at least partially within the chamber;
 a propellant disposed within the chamber;
 a piston disposed within the chamber, wherein the needle is coupled to the piston, wherein the piston is configured to slidably move within the chamber, wherein the piston includes a vent configured to allow gases produced by ignition of the propellant to vent through the piston; and
igniting the propellant to slidably move the piston within the chamber to drive the needle into skin to form a puncture in the skin.

18. The method of claim 17, wherein the system further comprises:
a suction source; and
a seal, wherein the seal is coupled to the suction source such that the seal receives suction provided by the suction source, wherein igniting the propellant to slidably move the piston within the chamber to drive the needle into skin further comprises driving the needle through the seal to form a hole in the seal when the seal is receiving suction provided by the suction source, and wherein the suction provided by the suction source is sufficient to draw blood from the formed puncture in the skin through the formed hole in the seal.

19. The method of claim 18, wherein the system further comprises a sensor, wherein the suction provided by the suction source is sufficient to draw blood through the formed hole in the seal to the sensor, and further comprising:
operating the sensor to detect a property of blood to which the sensor is exposed.

20. The method of claim 17, wherein the system further comprises a blood storage element, wherein the suction provided by the suction source is sufficient to draw blood through the formed hole in the seal to the blood storage element, wherein the blood storage element is configured to store blood drawn by the suction source to the blood storage element, and further comprising:
providing the blood stored by the blood storage element to a sensing device; and
operating the sensing device to detect a property of the blood provided to the sensing device.

* * * * *